US012758798B2

(12) United States Patent
Levy

(10) Patent No.: US 12,758,798 B2
(45) Date of Patent: Oct. 13, 2026

(54) ULTRASOUND AUTOFOCUSING FOR SHORT-PULSE PROCEDURES

(71) Applicant: Insightec, Ltd., Tirat Carmel (IL)

(72) Inventor: Yoav Levy, Tirat Carmel (IL)

(73) Assignee: INSIGHTEC, LTD., Tirat Carmel (IL)

( * ) Notice: Subject to any disclaimer, the term of this patent is extended or adjusted under 35 U.S.C. 154(b) by 0 days.

(21) Appl. No.: 18/709,759

(22) PCT Filed: Nov. 9, 2022

(86) PCT No.: PCT/IB2022/000682
§ 371 (c)(1),
(2) Date: May 13, 2024

(87) PCT Pub. No.: WO2023/084307
PCT Pub. Date: May 19, 2023

(65) Prior Publication Data

US 2025/0001215 A1 Jan. 2, 2025

Related U.S. Application Data

(60) Provisional application No. 63/278,867, filed on Nov. 12, 2021.

(51) Int. Cl.
*A61N 7/00* (2006.01)

(52) U.S. Cl.
CPC ........ *A61N 7/00* (2013.01); *A61N 2007/0039* (2013.01); *A61N 2007/0078* (2013.01)

(58) Field of Classification Search
CPC .............. A61N 7/00; A61N 2007/0039; A61N 2007/0078; A61N 7/02; A61N 2007/0086; A61N 2007/0095
See application file for complete search history.

(56) References Cited

U.S. PATENT DOCUMENTS 10,765,892 B1 * 9/2020 Vitek ..................... A61B 34/10
2004/0135992 A1 * 7/2004 Munro .................... G01S 7/483 356/4.01
2017/0100091 A1 * 4/2017 Eigil ...................... A61B 8/085
2018/0011193 A1 * 1/2018 Brown ................ G01S 15/8915
2018/0206816 A1 * 7/2018 Prus ..................... A61B 8/5215
(Continued)

FOREIGN PATENT DOCUMENTS

WO 2021/123906 A1 6/2021

OTHER PUBLICATIONS

Search Report and Written Opinion for related International Patent Application No. PCT/IB2022/000682, 13 pages, dated May 2, 2023.

*Primary Examiner* — Bo Joseph Peng
(74) *Attorney, Agent, or Firm* — Morgan, Lewis & Bockius LLP

(57) ABSTRACT

In an ultrasound system, echo focusing is performed to align ultrasound pulse peaks, establishing the phase delay required for each ultrasound transducer element, and the temporal displacements among pulses are determined using, for example, time-of-flight (ToF) measurements. The combined approach aligns the phases and the envelopes of pulses delivered by the active transducer elements that contribute energy during treatment. Moreover, it permits long pulses to be used for phase alignment in the preparatory stage and perfectly aligned short pulses in the sonication stage.

20 Claims, 4 Drawing Sheets

(56) References Cited

U.S. PATENT DOCUMENTS

| | | | | |
|---|---|---|---|---|
| 2019/0030375 | A1* | 1/2019 | Zachar | A61N 7/02 |
| 2019/0175954 | A1* | 6/2019 | Levy | A61B 8/4494 |
| 2019/0178851 | A1* | 6/2019 | Prus | G01N 29/07 |
| 2019/0308038 | A1* | 10/2019 | Prus | A61B 8/0808 |
| 2020/0085409 | A1* | 3/2020 | Grinfeld | A61N 7/00 |
| 2025/0001215 | A1* | 1/2025 | Levy | A61N 7/00 |

* cited by examiner

ULTRASOUND AUTOFOCUSING FOR SHORT-PULSE PROCEDURES

CROSS-REFERENCE TO RELATED APPLICATIONS

This application is a 371 National Stage Entry of International Patent Application No. PCT/IB2022/000682 filed Nov. 11, 2022, which claims priority to, and the benefit of, U.S. Ser. No. 63/278,867, file on Nov. 12, 2021, the entirety of which are hereby incorporated by reference.

FIELD OF THE INVENTION

The present invention relates, generally, to systems and methods for ultrasound focusing and, more particularly, to aufocusing using microbubbles.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, thereby eliminating the need for invasive surgery, targeted drug delivery, control of the blood-brain barrier, lysing of clots, and other surgical procedures. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

The noninvasive nature of ultrasound surgery is particularly appealing for the treatment of brain tumors. However, the human skull has been a barrier to the clinical realization of ultrasound therapy. Impediments to transcranial ultrasound procedures include strong attenuation and the distortions caused by irregularities in the skull's shape, density, and sound speed, which contribute toward destroying the focus and/or decreasing the ability to spatially register received diagnostic information.

To overcome difficulties associated with the human skull, one conventional approach measures phase shifts resulting from travel of an ultrasound beam through the skull and subsequently adjusts ultrasound parameters to account for the aberrations caused at least in part by the skull. For example, a minimally invasive approach uses receiving probes designed for catheter insertion into the brain to measure the amplitude and phase distortion caused by the skull. Catheter insertions, however, still require surgery, which can be painful and can create a risk of infection.

An alternative, completely noninvasive approach uses X-ray computed tomography (CT) images, rather than receiving probes, to predict the wave distortion caused by the skull. In practice, however, computations of the relative phases alone may too be imprecise to enable high-quality focusing. For example, when ultrasound is focused into the brain to treat a tumor, the skull in the acoustic path may cause aberrations that are not readily ascertainable. In such situations, treatment is typically preceded by a focusing procedure in which an ultrasound focus is generated at or near the target, the quality of the focus is measured (using, e.g., thermal imaging or acoustic radiation force imaging (ARFI)), and experimental feedback is used to adjust the phases of the transducer elements to achieve sufficient focus quality.

The preceding focusing procedure, however, may take a substantial amount of time, which may render it impracticable or, at the least, inconvenient for a patient. In addition, ultrasound energy is inevitably deposited into the tissue surrounding the target during the procedure, thereby potentially damaging healthy tissue. While the effect of pre-therapeutic sonications may be minimized by employing an imaging technique that requires only low acoustic intensity (e.g., ARFI), it is generally desirable to limit the number of sonications prior to treatment.

Another approach to estimating the wave aberrations resulting from the skull involves use of an acoustic reflector (e.g., a small cloud of microbubbles) in the focus zone. By transmitting the ultrasound waves to the microbubbles and receiving reflections therefrom, the amplitudes and/or phases associated with the reflected ultrasound can be determined; based thereon, the transducer parameters (e.g., phase shifts and/or amplitudes) can be adjusted to compensate for the aberrations caused at least in part by the skull. As described in PCT Appl. No. WO 2021/123906, filed on Dec. 18, 2020, the entire disclosure of which is hereby incorporated by reference, an optimization approach may be implemented to determine one or more optimal values of one or more parameters (e.g., the acoustic power, microbubble concentration, etc.) associated with an ultrasound transducer and/or the acoustic reflector. Because the optimization approach can be performed on each patient, the obtained optimal values are patient-specific; as a result, adjustments of the ultrasound parameters (e.g., amplitudes, phases, etc.) using the autofocusing procedure for compensating the aberrations resulting from the patient-specific intervening tissue may be more accurately determined, thereby advantageously improving the focusing properties and treatment efficiency at the target region.

While this echo-based approach to autofocusing is advantageous for ultrasound procedures using long pulses (e.g., high-intensity focused ultrasound (HIFU) therapy as described in the '3906 application), it may be less effective when applied to procedures that use pulses whose spatial extents are short relative to the wavelength and the distance between the target and the transducer. One such procedure is histotripsy, which involves the delivery of acoustic energy in the form of short (generally less than 50 μsec), high-amplitude pulses that deliver relatively low total energy at high peak pressure. This induces brief cavitation to mechanically rupture targeted tissue. Cavitation occurs when a sufficiently negative pressure is applied to tissue to cause microbubble formation from fluid vaporization and release of dissolved gas. Once formed, the microbubbles exhibit highly dynamic patterns of oscillation and inertial collapse that produce cellular and tissue disruption. Whereas lesioning applications such as HIFU are sensitive to the amount of energy reaching the target, histotripsy is more sensitive to the negative peak pressure. Therefore, for histotripsy, it is important to synchronize from end to end the ultrasound pulses converging at the target so that they substantially overlap.

Because echo-based autofocusing relies on constructive phase interference between transmitted and reflected pulses, there is no way to guarantee that the entire pulse is aligned among transducer elements; as a result, the points of convergence among transducer emissions may be displaced by a multiple of the ultrasound wavelength. This is not problematic for HIFU procedures, because phase alignment of long pulses ensures that energy is delivered at peak power and any fractional pulse misalignment will not significantly degrade the overall energy deposit. But it is, as noted, problematic for histotripsy and similar procedures.

SUMMARY

In accordance with embodiments of the invention, echo focusing is performed to align pulse peaks, establishing the phase delay required for each ultrasound transducer element, and the temporal displacements among pulses are determined using, for example, time-of-flight (ToF) measurements. The combined approach aligns the phases and the envelopes of pulses delivered by the active transducer elements that contribute energy during treatment. Moreover, it permits long pulses to be used for phase alignment and short pulses, as will be used during the therapeutic procedure, to be used for envelope alignment. For example, ToF measurements may be used to roughly align short pulses, following which long pulses are used for phase alignment. Short treatment pulses will then be aligned in phase and in spatial extent.

As used herein, unless otherwise indicated, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
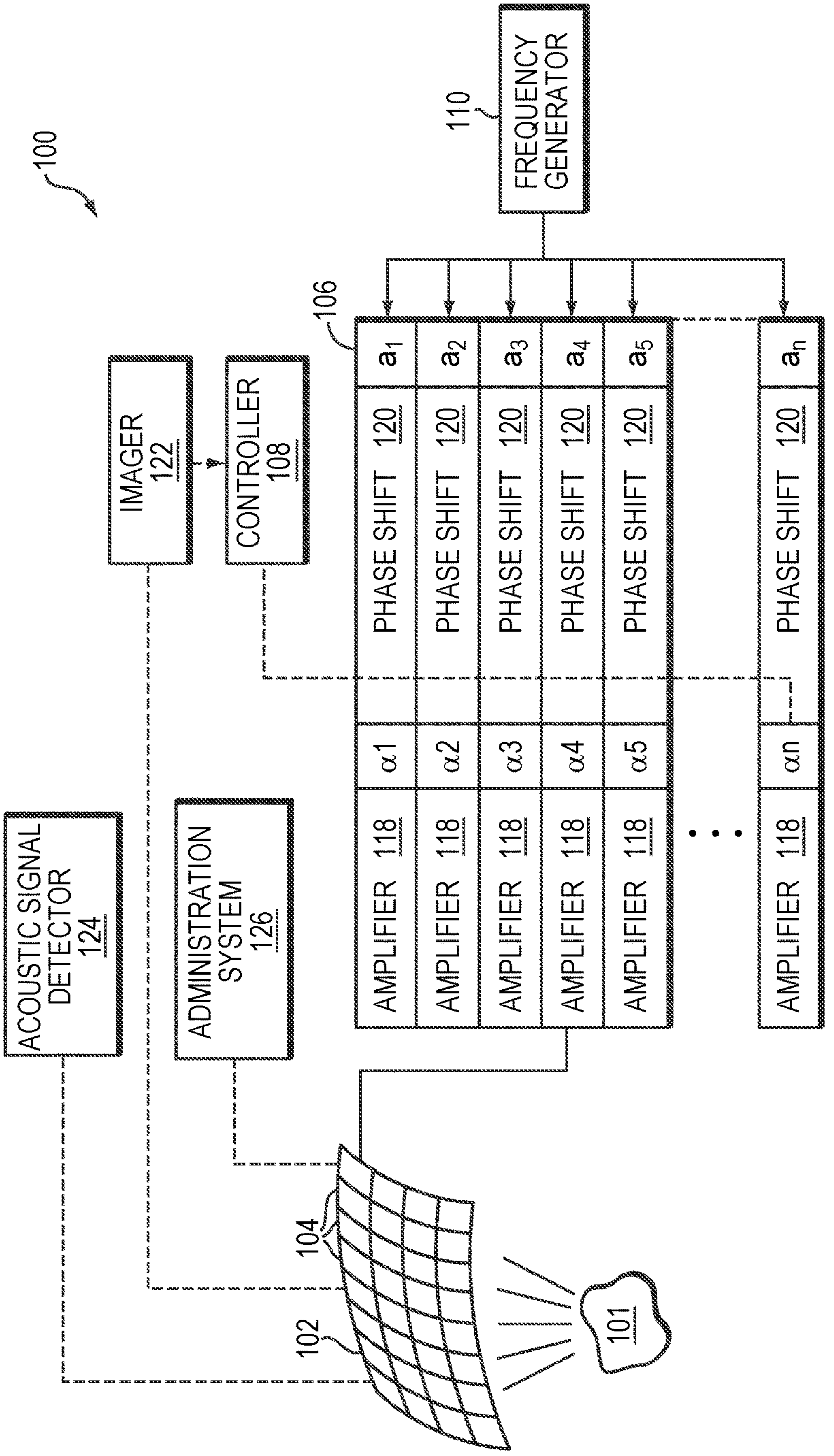
FIG. 1 schematically depicts an exemplary ultrasound system in accordance with various embodiments.

FIG. 1 illustrates an exemplary ultrasound system 100 for focusing ultrasound beams through the skull onto a target region 101 within a patient's brain. One of ordinary skill in the art, however, will understand that the ultrasound system 100 described herein may be applied to any part of the human body, and that it may be a HIFU system, an imaging system, a histotripsy system, or other ultrasound system. In various embodiments, the system 100 includes a phased array 102 of transducer elements 104, a beamformer 106 driving the phased array 102, a controller 108 in communication with the beamformer 106, and a frequency generator 110 providing an input electronic signal to the beamformer 106.

The array 102 may have a curved (e.g., spherical or parabolic) shape suitable for placement on the surface of the skull or a body part other than the skull, or may include one or more planar or otherwise shaped sections. Its dimensions may vary, depending on the application, between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase delay circuit 120; each drive circuit drives one of the transducer elements 104. The beamformer 106 receives a radio frequency (RF) input signal, typically in the range from 0.1 MHz to 1.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through inhomogeneous tissue (e.g., the patient's skull) onto the target region (e.g., a region in the patient's brain). Via adjustments of the amplification factors and/or the phase shifts, a desired shape and intensity of a focal zone may be created at the target region.

The amplification factors and phase shifts may be computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, to determine the frequency, phase shifts and/or amplification factors of the transducer elements 104. In certain embodiments, the controller computation is based on information about the characteristics (e.g., structure, thickness, density, etc.) of the skull and their effects on propagation of acoustic energy. In various embodiments, such information is obtained from an imager 122, such as a magnetic resonance imaging (MRI) device, a computer tomography (CT) device, a positron emission tomography (PET) device, a single-photon emission computed tomography (SPECT) device, or an ultrasonography device. The imager 122 may provide a set of two-dimensional images suitable for reconstructing a three-dimensional image of the skull from which thicknesses and densities can be inferred; alternatively, image acquisition may be three-dimensional. In addition, image-manipulation functionality may be implemented in the imager 122, in the controller 108, or in a separate device.

The system 100 may be modified in various ways within the scope of the invention. For example, the system may further include an acoustic signal detector (e.g., a hydrophone) 124 that measures transmitted or reflected ultrasound, and which may provide the signals it receives to the controller 108 for further processing. The reflection and transmission signals may also provide an alternative or additional source for determining the phase shifts and/or amplification factors or feedback for the phase and amplitude adjustments of the beamformer 106 as further described below. The system 100 may contain a positioner for arranging the array 102 of transducer elements 104 with respect to the patient's skull. In order to apply ultrasound therapy to body parts other than the brain, the transducer array 102 may take a different (e.g., cylindrical) shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

Figure 2A:
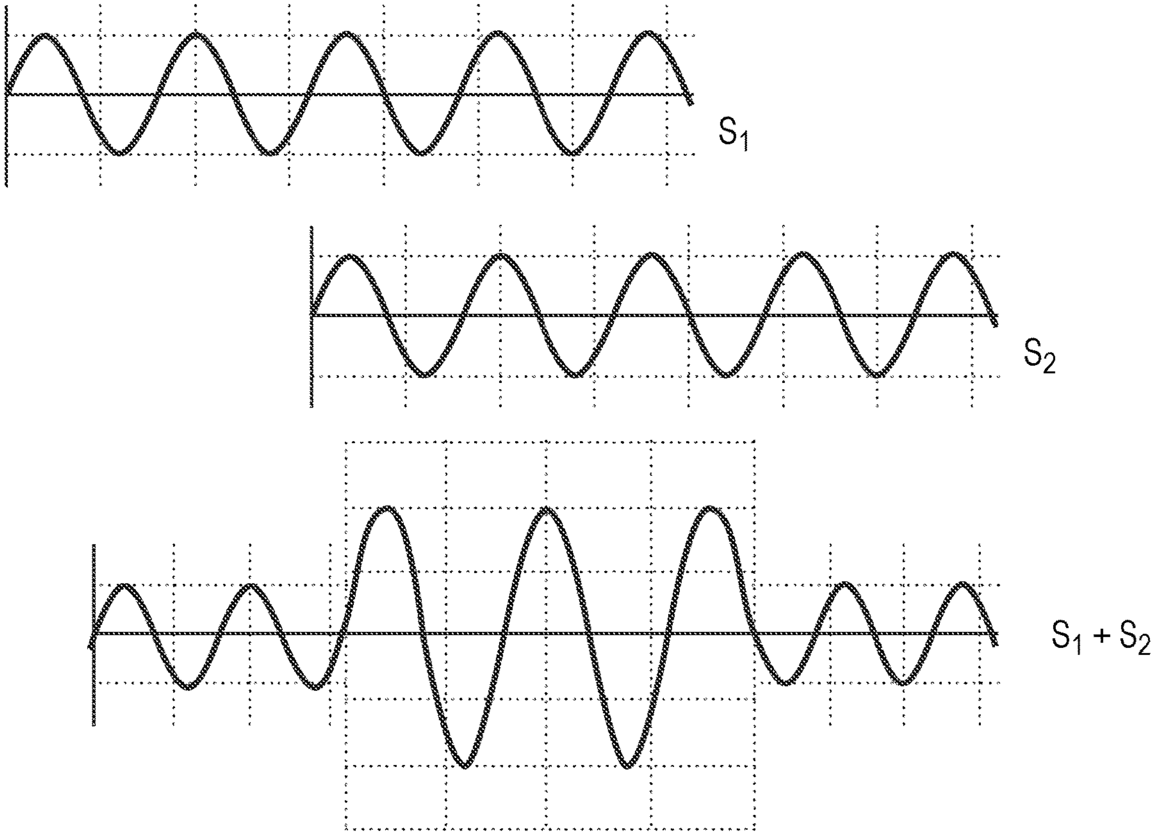
FIG. 2A illustrates constructive interference between a pair of short acoustic pulses.

The problem of focusing with short pulses may be understood with reference to FIG. 2A. Two acoustic signals $S_1$ and $S_2$ are emitted by different transducer elements 104 (FIG. 1). For explanatory purposes, each of the signals $S_1$ and $S_2$ is shown with a pulse envelope of just over four cycles or periods, but a "short" pulse for purposes hereof has a length of one to 50 cycles; a "long" pulse has a length greater than 50 cycles. Typical histotripsy pulses have durations of 3 to 30 cycles. The signals $S_1$ and $S_2$ are offset in time but, where they overlap, their phases are aligned so that, when added, the interference is constructive. If the pulses $S_1$ and $S_2$ were much longer and the region of overlap at the target large relative to the temporal offset, constructive interference would dominate; consequently, most of the pulse energy would be delivered to the target at peak power. But if, as illustrated, the pulses are short and the region of non-overlap large relative to the pulse envelope, only a minor portion of the energy is delivered at peak power. The displacement between pulses may even exceed the pulse length, in which case there will be no overlap between the pulses.

Conceptually, even short pulses could be aligned if the duration of constructive interference could be measured accurately. For example, the timing of a first pair of transducer elements 104 could be adjusted until the period of peak power (as measured by energy deposition) coincides with the pulse duration, indicating complete envelope and phase alignment. This procedure could be repeated by pairing one of the adjusted transducer elements with a third element, adjusting the relative timing, and conforming the timing of the other previously adjusted element thereto so that the envelopes of all three elements coincide at a target. Eventually the timing of all transducer elements could be brought into consistency this way so that all pulse envelopes fully overlap. This approach is challenging as a practical matter because the energy produced by constructively intefering ultrasound pulses is small relative to the ambient temperature, i.e., noise. Hence, embodiments of the present invention combine time-delay adjustment with phase adjustment. The time-delay adjustment brings the envelopes of signals $S_1$ and $S_2$ into rough alignment, e.g., coincident within a single wavelength (or, in some cases, within 20% of the pulse length). The phase adjustment brings the pulses into substantially full alignment. By "substantially full alignment" is meant that the envelopes align to within 80% of the pulse length and the phases align to within $\pi/5$ radian. As used herein, the term "time delay" means the difference in the acoustic propagation time between different transducer elements and a target; and the term "phase delay" means the phase difference between pulses from different transducer elements at a target.

Figure 2B:
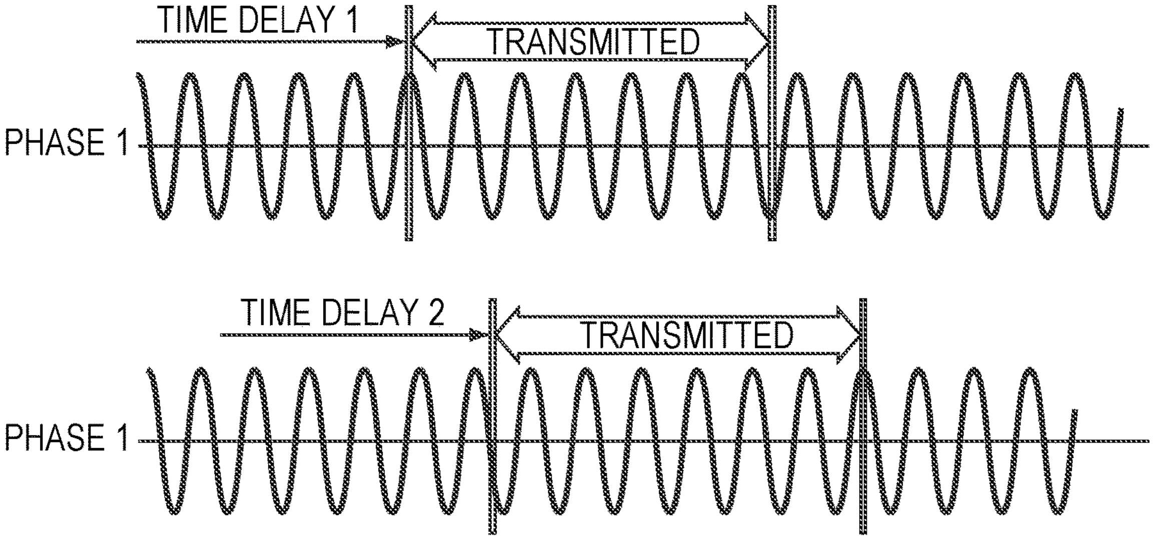
FIGS. 2B and 2C illustrate alternative modes of time-delayed pulse transmission.
Figure 2C:
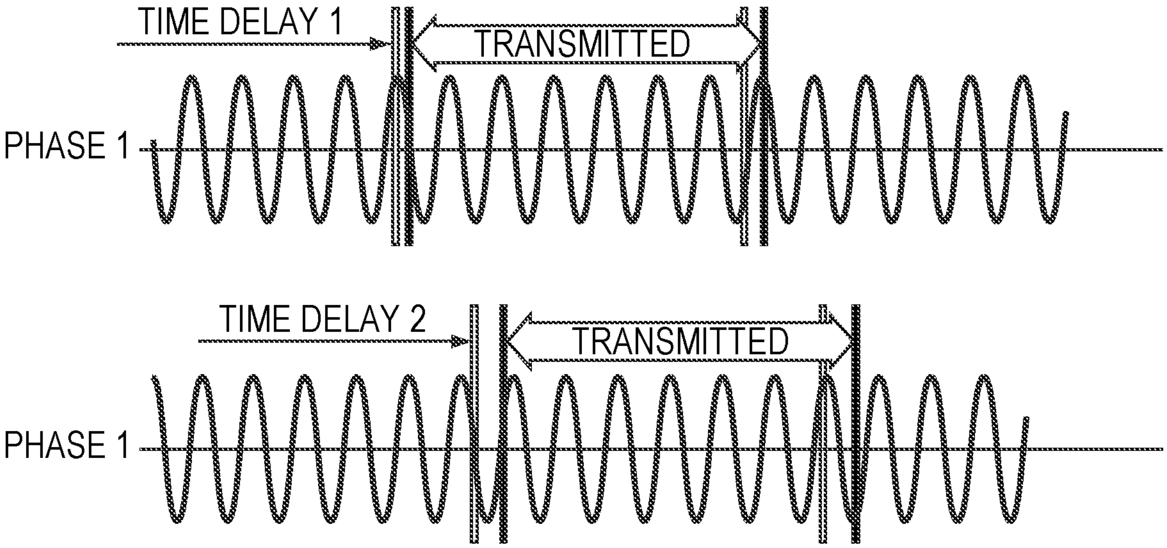

In practice, pulses can be viewed as windowed portions of a continuous signal generated by a signal generator, which is connected to a transmitting transducer element via a switch. As shown in FIGS. 2B and 2C, the element transmits during the TRANSMITTED window following its time delay, in effect cropping the signal to create the pulse. The relative signal phases (Phase 1 and Phase 2) are adjusted so that when the cropped pulses meet at the target, they are in phase, i.e., constructively interfere. As is conventional in signal processing, the window may be defined by a smoothing function such as a Hann or Hamming window. In FIG. 2B, the cropping is arbitrary, while in FIG. 2C, the cropping begins at a signal peak or minimum, which may be easier to implement for some hardware configurations.

Figure 3:
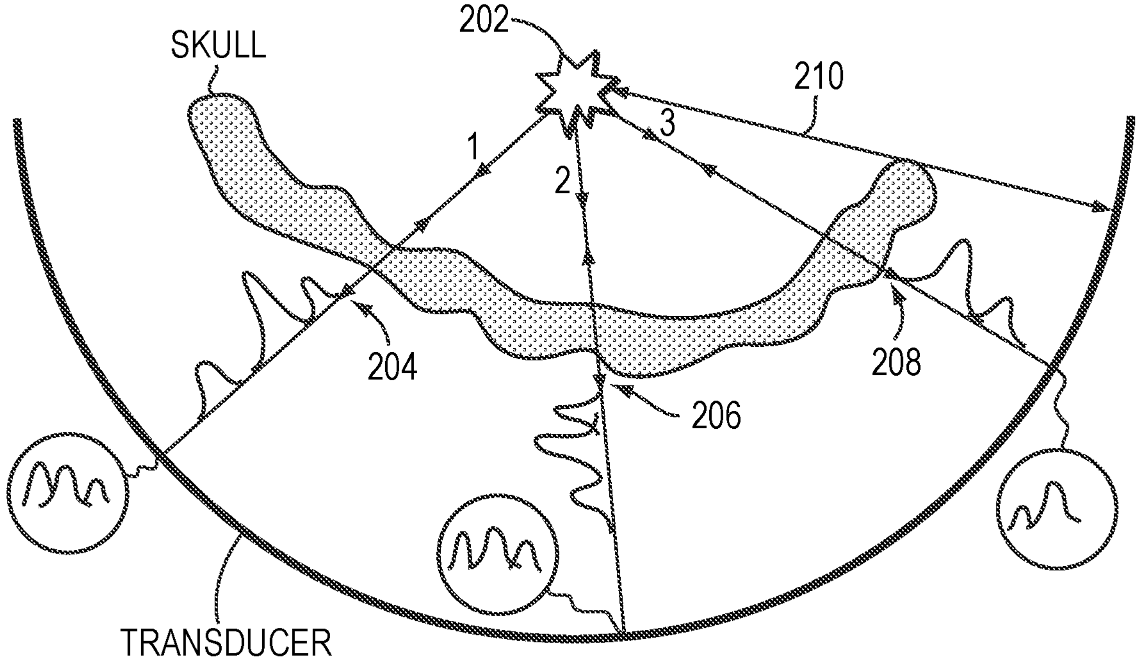
FIG. 3 depicts one or more transient acoustic reflectors located in proximity to one or more target regions in accordance with various embodiments.

With reference to FIGS. 1 and 3, in various embodiments, both the time-delay and phase adjustments may be carried out using one or more transient reflectors 202 (e.g., microbubbles), which may be introduced in proximity to (e.g., less than 5 mm away) a target region 101 in a subject (human, animal, or an ultrasound phantom). The microbubbles 202 may be generated by applying acoustic energy from the transducer elements 104 to the target 101. The microbubbles 202 can be formed due to the negative pressure produced by the propagating ultrasonic waves or when the heated liquid at the target ruptures and is filled with gas/vapor. Because of their encapsulation of gas, the microbubble(s) 202 may act as reflectors of the ultrasound waves and transmit coherent omnidirectional signals 204-208 to the transducer 102; the reflection signals 204-208 can be substantially concurrently detected by the transducer elements 104 and/or acoustic signal detector 124 associated therewith as further described below. Based on analysis of the reflection signals, the controller 108 may obtain time-delay and phase information for adjusting the transducer elements 104, thereby compensating for differences in path length to the target 202 as well as aberrations caused by the intervening tissue located between the transducer elements 104 and target 101 (with reference to FIG. 3, located between the transducer and the target 202 as depicted by arrow 210). Approaches to generating microbubbles utilizing ultrasound waves are provided, for example, in U.S. Patent Publication No. 2019/0308038, the entire contents of which are incorporated herein by reference. In a time-delay measurement, the time of flight of an acoustic pulse represents the time of travel to, and back from, a target. A pulse emitted by one transducer element may be detected, as reflections from the target, by multiple transducer elements. Dividing the time of flight measured by each element by two gives the propagation time, and differences in the propagation time across elements represents the time delay therebetween. Alternatively, as described below, the time of flight can be estimated based on the relative geometries of the transducers and a physical model, and once again, dividing by two provides the time delay.

Figure 4A:
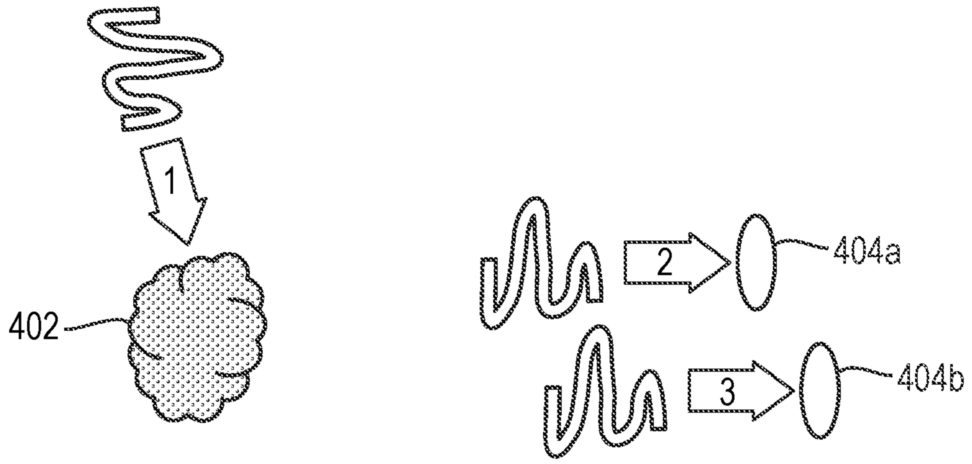
FIGS. 4A and 4B schematically illustrate different modes of measuring and computing time delays among transducer elements.
Figure 4B:
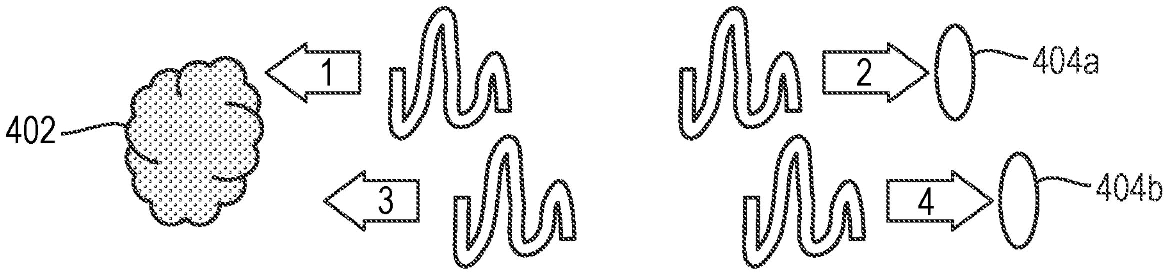

In greater detail, as shown in FIG. 4A, an acoustic pulse (1) is transmitted by a transducer element (not shown) to a target 402. The reflection reaches different transducer elements at different times—in particular, the reflection reaches the transducer element 404*a* at a time $t_1$ and transducer element 404*b* at a later time $t_2$. The time delay of the transducer element 404*b* relative to the element 404*a* is $t_2-t_1$. The time of flight is unknown and the time delay is computed based on the difference in time of arrival. In FIG. 4B, the transducer element 404*a* emits a pulse (1) at time $t_1$ and records the arrival of the reflection (2) at time $t_2$. The transducer element 404*b* emits a pulse (3) at time $t_3$ and records the arrival of the reflection (4) at time $t_4$. The time delay of the transducer element 404*b* relative to the element 404*a* is given as $$\frac{(t_4-t_3)-(t_2-t_1)}{2}$$

where $(t_2-t_1)/2$ is the time of flight from the element 404*a* to the target 402 and $(t_4-t_3)/2$ is the time of flight from the element 404*b* to the target 402.

Additionally or alternatively, the acoustic reflector 302 may be introduced into the patient's body intravenously; the transient reflector may either be injected systemically into the patient or locally into the target region 101 using an administration system 126. For example, the transient reflector 302 may include or consist of one or more microbubbles introduced into the patient's brain in the form of liquid droplets that subsequently vaporize to form the microbubbles; or as gas-filled bubbles entrained within a liquid carrier, e.g., a conventional ultrasound contrast agent. Alternatively, other substances suitable for cavitation nucleation can be administered instead of bubbles (see, e.g., www.springer.com/cda/content/document/cda_download-document/9783642153426-c1.pdf?SGWID=0-0-45-998046-p174031757).

Typically, an automated administration system may be operated by the controller 108 or a dedicated controller associated with the administration system. For example, analysis of the reflection signals may cause the controller 108 to operate the administration device 126 so as to increase or decrease the amount of acoustic reflectors introduced intravenously and/or adjust the type of microbubbles. Alternatively or additionally, analysis of the reflection signals may cause the controller 108 to operate the transducer 102 so as to increase or decrease, via induced cavitation, the amount of circulating or localized microbubbles; an increased acoustic power, for example, may reduce the number of microbubbles by causing their collapse. Alternatively, the administration system 126 may be manual, such as a simple syringe. In the case of manual administration, analysis of the reflection signals may cause the controller 108 to determine an adjustment to the amount of acoustic reflectors introduced intravenously and/or the type of microbubbles, and to operate the transducer 102 based on this determination. Approaches for providing acoustic reflectors to the target region using suitable administration systems are described, for example, in PCT Publication No. WO 2019/116095, the entire disclosure of which is hereby incorporated by reference.

In one embodiment, the administration system 126 introduces a relatively low concentration (e.g., 5% of the concentration used for standard imaging) of microbubbles into the target 101 such that the acoustic reflections appear to originate from a point target (e.g., having a size less than that of a quarter of the sonication wavelength) such as a single microbubble (as opposed to a cloud of microbubbles). This is because reflection signals from a cloud of microbubbles may be incoherent and/or exhibit artifacts due to low SNRs and/or vibrations from the multiple microbubbles; as a result, analysis of the reflection signals from the cloud of microbubbles may be inaccurate and adjustment of the transducer parameters based thereon may be insufficient to account for the aberrations caused by the intervening tissue. In addition, analysis of the reflection signals from the cloud of microbubbles may be computationally expensive and time-consuming. On the other hand, the microbubble concentration is preferred to be sufficiently high to cause significant interaction with the ultrasound waves, thereby providing detectable reflections for performing the autofocusing procedure. Thus, in one embodiment, prior to the autofocusing procedure, an initial microbubble concentration introduced to the target region is first empirically predetermined based on a pre-clinical study, a pre-treatment procedure, and/or from known literature. Thereafter, an optimization approach is performed to determine the optimal microbubble concentration, acoustic power and/or other parameters associated with the ultrasound transducer and/or microbubbles for facilitating the autofocusing procedure as further described below.

In an exemplary case, the initial microbubble concentration contains 1.3 milliliter (mL) of a microbubble suspension (acquired from, for example, DEFINITY) diluted in 500 mL of water; the infusion is then introduced into the patient's body with a drip rate of 1 mL/minute. After introduction of the microbubbles, the controller 108 may activate at least some of the transducer elements 104 to sequentially generate multiple foci at various sonication locations, e.g., in proximity to the target region 101 (e.g., less than 5 mm away) or at the target region 101, and each location may have one or more transient reflectors 302 associated therewith. In various embodiments, the sonication locations are determined based on the image(s) acquired by the imager 122 and/or the ultrasound transducer 102. For example, the imager 122 may acquire images of the target and/or non-target regions; and the ultrasound transducer 102 may acquire images of the transient reflector(s) 302 in the target/non-target regions based on the reflection signals therefrom. Based on the acquired images of the target/non-target regions and the transient reflectors associated therewith, the controller 108 may select the sonication locations. Approaches to acquiring images of the transient reflector(s) using the reflection signals therefrom are provided, for example, in U.S. Ser. No. 62/949,597, filed on Dec. 18, 2019, the entire disclosure of which is hereby incorporated by reference.

In some embodiments, upon collection of the reflection signals from all (or at least some) of the sonication locations, an initial signal-processing procedure is performed to select signals that are more likely to be from the transient reflectors. This approach may advantageously eliminate (or at least reduce) usage of reflections from background reflectors (e.g., the skull), thereby improving the accuracy and reliability of the focusing properties determined based on the measured reflection signals. In an exemplary signal-processing procedure for selecting reflection signals, for each of a series of sonication locations, the controller 108 compares the measured reflection signals from two consecutive measurements to determine the difference therebetween (or a "differential" signal). As described in U.S. Ser. No. 17/312,145, filed on Jun. 9, 2021, the entire disclosure of which is hereby incorporated by reference, the differential signals may be used to distinguish background signals from signals that contain echoes from transient reflectors; once the background signals have been isolated (e.g., by subtractive filtering) from the mixed signals, they may be used for autofocusing.

In particular, the coincident location of all (or at least some) of the transient reflectors having sufficiently consistent reflection signals may be used as a basis for ToF distance estimation. The transducer elements 104 that will be employed in the therapeutic procedure are activated to produce short ultrasound pulses singly, simultaneously, or in groups, and the controller 108 measures elapsed time until a reflection signal is detected at each activated transducer element. The time differences correspond to differences in distance between transducer elements and the transient reflector, and these differences are used as delays applied to each of the beamformer driver circuits 106; short pulse signals applied by the controller 108 to the driver circuits thereby arrive as acoustic pulses at the target location at substantially the same time.

It is possible to ascertain the location of the transient reflector 302 using the imager 122, which may be a CT device, by analyzing the acquired CT images of the target region and/or the non-target region surrounding the target region. It is not, however, necessary to know or estimate the location of the transient reflector 302 in order to establish the relative delays among transducer elements, so long as it is certain that all transducers are receiving (and the controller 108 is making and storing elapsed time measurements based on) the same reflection signal. This may be accomplished as described in the '3906 application, which describes discriminating among return signals to select ones that emanate from a single reflector. Discrimination may involve selection based on consistency—e.g., reflection signals may be considered to have sufficient consistency when the value of a consistency function of the phase delays (or travel times) associated with the reflection signals is maximized or exceeds a predetermined threshold such as 40%).

On the other hand, it is possible to use a known target location to estimate the time delay for each of the transducer elements. This may be accomplished by computationally representing the positions of the target and all transducer elements in a common spatial coordinate reference frame and estimating the distance from the target to each transducer element. The average speed of sound along each path from a transducer element to the target may be estimated based on the types of tissue along the path as identified by the imager 122. Dividing each measured path length by the associated speed of sound gives the propagation time of an acoustic signal. A typical propagation time for a path length of 15 cm is 0.1 millisecond. In practice, the propagation time for targets sonicated by a transducer as shown in FIG. 3, assuming a transducer curvature radius of 15 cm, can be from 0 to 0.2 millisecond, i.e., the time delay—which is the difference in propagation time between elements-might be up to 0.2 millisecond). A physical model may be more elaborate than a simple tissue model. As described in U.S. Ser. No. 16/314,985, the entire disclosure of which is hereby incorporated by reference, a physical model may include the geometries of the transducer elements, their locations and orientations relative to the target, and/or relevant material properties (e.g., the energy absorption of the tissue or the speed of sound at the employed frequency) along the beam path. Alternatively or additionally, the power levels and/or relative phases may be estimated based on the transmitted and/or reflected ultrasound measured either prior to treatment or during treatment (e.g., during treatment setup). The physical model may, alternatively or in addition, specify material properties along the beam path affecting the speed of sound and/or prior measurements of transmitted and/or reflected ultrasound propagation.

Once these delays are computed and stored, their application to the drivers 106 will ensure that the resulting acoustic signals are in substantially full alignment. In addition, it is possible to use much longer pulses to fully align the acoustic signals. As described in the '145 application, the controller 108 may record the amplitude and/or phase associated with each transducer element measuring a reflection signal and shift the phase of the driver signal until any artifacts in the measured reflections are eliminated or reduced below a threshold. The pulses may be long enough that the acoustic signal traverses the complete path from transducer element to reflector and back before the pulse is even complete. This may involve a pulse duration of 10, 50 or 100 or more cycles. In effect, such long pulses are essentially continuous, simplifying the phase shift since there are no significant temporal gaps within the signal; and moreover, because the signal-to-noise ratio grows with the length of the pulse (for signals with the same amplitude), longer pulses allow for more accurate phase alignment simply by suppressing noise artifacts.

One of ordinary skill in the art will understand that variations in the autofocusing approach described above are possible and are thus within the scope of the present invention. For example, it may not be necessary to activate a majority of the transducer elements 104 for performing autofocusing using the transient reflector(s) as described herein, and the number of transducer elements activated in each sonication of the sonication series may vary. For example, a fraction of the transducer elements 104 (e.g., 10%) may be selected to transmit and/or receive ultrasound waves in a first sonication associated with the first sonication location. The computed phase differences associated with the selected transducer elements may then be interpolated, extrapolated or processed using any suitable estimation approach to obtain the phase differences associated with unselected transducer elements. In the next sonication, a fraction of the previously unselected transducer elements may be used to repeat the autofocusing steps—i.e., transmitting ultrasound waves to the transient reflector(s) based on the interpolated (or extrapolated) phase differences and receiving reflections from the transient reflector. The selected transducer elements in the current sonication may or may not include the selected transducer elements in the precedent sonication(s) and the number of selected elements may be different in each sonication.

In general, functionality for performing autofocusing of ultrasound beams using reflection signals from one or more transient acoustic reflectors may be structured in one or more modules implemented in hardware, software, or a combination of both, whether integrated within a controller of the imager 122, an ultrasound system 100, and/or an administration system 126, or provided by a separate external controller or other computational entity or entities. Such functionality may include, for example, causing one or more transient acoustic reflectors to be introduced in the patient's body in proximity to a target region, identifying multiple sonication locations near or at the target region and sequentially generating a focus at each of the sonication locations, measuring ultrasound signals reflected from the transient reflector(s) associated with each of the sonication locations, comparing the measured reflection signals between two consecutive measurements to determine a difference therebetween (or a differential signal), computing an amplitude ratio between two consecutive differential signals, comparing the amplitude ratio to a predetermined threshold, selecting the reflection signals based on the comparison of the amplitude ratio, selecting a portion (e.g., a time window) of each of the measured reflection signals, determining the amplitude and/or phase associated with the selected portion of each reflection signal, determining a difference between the amplitudes and/or phases associated with the selected portions of the reflection signals in the two consecutive measurements, determining a noise level associated with the measured reflection signals, selecting the reflection signals based on the difference associated with the selected portions of the reflection signals and the noise level, selecting two of the reflection signals measured by a transducer element, determining consistency between the selected reflection signals, computationally shifting the location of one transient acoustic reflector to coincide with the location of another transient acoustic reflector, determining the parameter value associated with the transducer element based on the travel times/phases associated with the reflection signals, comparing the coincident location against a sonication location estimated using other approach(es), computationally shifting the coincident location to coincide with the sonication location estimated using other approach(es) and then computationally updating the parameter value of the transducer element, and activating the transducer element based on the determined/updated parameter values.

In addition, the ultrasound controller, the imager and/or the administration system may include one or more modules implemented in hardware, software, or a combination thereof. For embodiments in which the functions are provided as one or more software programs, the programs may be written in any of a number of high level languages such as PYTHON, FORTRAN, PASCAL, JAVA, C, C++, C #, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors. The term "controller" used herein broadly includes all necessary hardware components and/or software modules utilized to perform any functionality as described above; the controller may include multiple hardware components and/or software modules and the functionality can be spread among different components and/or modules.

Certain embodiments of the present invention are described above. It is, however, expressly noted that the present invention is not limited to those embodiments; rather, additions and modifications to what is expressly described herein are also included within the scope of the invention.

What is claimed is:

1. A system for focusing an ultrasound transducer, the system comprising:

an ultrasound transducer comprising a plurality of transducer elements for providing a series of sonications to at least one target region; and a controller configured to:

obtain, for each of at least two transducer elements, an acoustic propagation time characterized by an amount of time it takes for an acoustic pulse to propagate from a respective transducer element to a target region;

calculate acoustic propagation time differences based on differences between the acoustic propagation times corresponding to the at least two transducer elements with respect to the target region;

cause the plurality of transducer elements to transmit test acoustic pulses to an acoustic reflector located at or proximate to the target region;

calculate phase delays for the plurality of transducer elements based on the test acoustic pulses; and sonicate the target region by driving the plurality of transducer elements to transmit sonicating acoustic pulses using (i) the acoustic propagation time differences to offset emission timing among the plurality of transducer elements and (ii) the phase delays to phase-shift the sonicating acoustic pulses of the plurality of transducer elements relative to one another.

2. The system of claim 1, wherein:

the test acoustic pulses are longer than the sonicating acoustic pulses; and the sonicating acoustic pulses are short pulses having a length no greater than 50 cycles.

3. The system of claim 1, wherein the controller is configured to obtain the propagation time differences by:

transmitting a test acoustic pulse to a second acoustic reflector; and measuring differences in time of arrival, at two or more transducer elements, of reflections of the test acoustic pulse from the second acoustic reflector.

4. The system of claim 3, wherein the second acoustic reflector is a transient acoustic reflector or a microbubble.

5. The system of claim 1, wherein the controller is configured to obtain the propagation time differences by:

transmitting a first test acoustic pulse to a second acoustic reflector from a first transducer element;

transmitting a second test acoustic pulse to the second acoustic reflector from a second transducer element; and measuring differences in time of flight of reflections of the first and second test acoustic pulses from the second acoustic reflector at the first and second transducer elements, respectively.

6. The system of claim 1, wherein the controller is configured to obtain the propagation time differences for at least two transducer elements by:

computationally representing the target region and the transducer elements in a common spatial coordinate reference frame; and estimating the propagation time differences based on the common spatial coordinate reference frame and a physical model.

7. The system of claim 6, wherein the physical model comprises:

an estimated distance from the target region to each transducer element based on at least one image; and an average speed of sound between the target region and the transducer elements, the propagation time differences being estimated based at least in part on the estimated distances and the average speed of sound.

8. The system of claim 6, wherein physical model includes at least one of:

geometries of the transducer elements, locations of the transducer elements and orientations of the transducer elements relative to the target region;

material properties along the beam path affecting the speed of sound; or prior measurements of transmitted and/or reflected ultrasound propagation.

9. The system of claim 1, wherein the first acoustic reflector is a transient acoustic reflector or a microbubble.

10. The system of claim 1, wherein the controller is further configured to:

select a subset of the test acoustic pulses based at least in part on consistency of arrival times and/or phases of reflection signals generated in response to the test acoustic pulses; and compute the phase delays based on the selected subset.

11. A method of focusing an ultrasound transducer comprising a plurality of transducer elements for providing a series of sonications to at least one target region, the method comprising the steps of:

obtaining, for each of at least two transducer elements, an acoustic propagation time characterized by an amount of time it takes for an acoustic pulse to propagate from a respective transducer element to a target region;

calculating acoustic propagation time differences based on differences between the acoustic propagation times corresponding to the at least two transducer elements with respect to the target region;

causing the plurality of transducer elements to transmit test acoustic pulses to an acoustic reflector located at or proximate to the target region;

calculating phase delays for the plurality of transducer elements based on the test acoustic pulses; and sonicate the target region by driving the plurality of transducer elements to transmit sonicating acoustic pulses using (i) the acoustic propagation time differences to offset emission timing among the plurality of transducer elements and (ii) the phase delays to phase-shift the sonicating acoustic pulses of the plurality of transducer elements relative to one another.

12. The method of claim 11, wherein:

the test acoustic pulses are longer than the sonicating acoustic pulses; and the sonicating acoustic pulses are short pulses having a length no greater than 50 cycles.

13. The method of claim 11, wherein the propagation time differences are obtained by steps comprising:

transmitting a test acoustic pulse to a second acoustic reflector; and measuring differences in time of arrival, at two or more transducer elements, of reflections of the test acoustic pulse from the second acoustic reflector.

14. The method of claim 13, wherein the second acoustic reflector is a transient acoustic reflector or a microbubble.

15. The method of claim 11, wherein the propagation time differences are obtained by steps comprising:

transmitting a first test acoustic pulse to a second acoustic reflector from a first transducer element;

transmitting a second test acoustic pulse to the second acoustic reflector from a second transducer element; and measuring differences in time of flight of reflections of the first and second test acoustic pulses from the second acoustic reflector at the first and second transducer elements, respectively.

16. The method of claim 11, wherein the propagation time differences are obtained, for at least two transducer elements, by steps comprising:

computationally representing the target region and the transducer elements in a common spatial coordinate reference frame; and computationally estimating the propagation time differences based on the common spatial coordinate reference frame and a physical model.

17. The method of claim 16, wherein the physical model comprises:

an estimated distance from the target region to each transducer element based on at least one image; and an average speed of sound between the target region and the transducer elements, the propagation time differences being estimated based at least in part on the estimated distances and the average speed of sound.

18. The method of claim 16, wherein physical model includes at least one of:

geometries of the transducer elements, locations of the transducer elements and orientations of the transducer elements relative to the target region;

material properties along the beam path affecting the speed of sound; or prior measurements of transmitted and/or reflected ultrasound propagation.

19. The method of claim 11, wherein the first acoustic reflector is a transient acoustic reflector or a microbubble.

20. The method of claim 11, further comprising the steps of:

selecting a subset of the test acoustic pulses based at least in part on consistency of arrival times and/or phases of reflection signals generated in response to the test acoustic pulses; and computing the phase delays based on the selected subset.

* * * * *